United States Patent [19]
Riggle et al.

[11] Patent Number: 5,622,912
[45] Date of Patent: Apr. 22, 1997

[54] SPROUT INHIBITION COMPOSITIONS COMPRISING CHLORPROPHAM AND SUBSTITUTED NAPHTHALENES AND METHODS OF USING SAME

[75] Inventors: Bruce D. Riggle, Eaton, Colo.; Ronald K. Schafer, Boise, Id.

[73] Assignee: Platte Chemical Company, Greeley, Colo.

[21] Appl. No.: 653,222

[22] Filed: May 24, 1996

[51] Int. Cl.$^6$ .......................... A01N 47/20; A01N 27/00
[52] U.S. Cl. ............................................ 504/143; 504/304
[58] Field of Search ..................... 504/143, 304

[56] References Cited

U.S. PATENT DOCUMENTS

| | | | |
|---|---|---|---|
| 2,341,868 | 9/1944 | Hitchcock et al. | 47/58 |
| 3,128,170 | 4/1964 | Plant | 71/2.6 |
| 4,078,480 | 3/1978 | Luck | 99/476 |
| 4,226,179 | 10/1980 | Sheldon, III et al. | 99/475 |
| 4,532,156 | 7/1985 | Everest-Todd | 427/220 |
| 4,735,134 | 4/1988 | Brouwer | 99/476 |
| 4,857,345 | 8/1989 | Sardo | 426/310 |
| 4,887,525 | 12/1989 | Morgan | 99/476 |
| 4,977,825 | 12/1990 | Morgan | 99/476 |
| 5,009,152 | 4/1991 | Morgan | 99/476 |
| 5,129,951 | 7/1992 | Vaughn et al. | 71/122 |
| 5,139,562 | 8/1992 | Vaughn et al. | 71/88 |
| 5,436,226 | 7/1995 | Lulai et al. | 504/291 |

FOREIGN PATENT DOCUMENTS

| | | |
|---|---|---|
| 8652829 | 1/1985 | Australia . |
| 1203394 | 4/1986 | Canada . |
| 0394961A2 | 10/1990 | European Pat. Off. . |
| 0394961A3 | 5/1991 | European Pat. Off. . |
| 63-179801 | 1/1987 | Japan . |
| WO88/08249 | 11/1988 | WIPO . |
| WO93/06724 | 4/1993 | WIPO . |

OTHER PUBLICATIONS

"Clean Crop Sprout NIP® 7A Sprout Nip," 1994 Specimen Label and Material Safety Data Sheet, Platte Chemical Co., 50 S. Main Street, Fremont, NE 68025-5697.

"Clean Crop Sprout NIP® Emulsifiable Concentrate," 1994 Specimen Label and Material Safety Data Sheet, Platte Chemical Co., 50 S. Main Street, Fremont, NE 68025-5697.

Shetty, Kiran K., et al., "Fine-Tuning Time For Inhibition," Potato Grower of Idaho, Dec. 1993, pp. 14-15.

Shetty, Kiran K., et al., "Controlling potato sprouting is most important factor—Applications vital," Potato Grower of Idaho, Sep., 1995, pp. 18-19.

Kleinkopf, Gale, et al., "CIPC Application to Potatoes in Long-Term Storage Examined," Potato Country, Feb., 1996, pp. 24-26.

Dennis, Frank G. "Dormancy: Manifestations and Causes". Chapter 20 in *Handbook of Plant and Crop Physiology*, Mohammad Pessarakli, ed. pp. 448-450. 1995.

*Primary Examiner*—S. Mark Clardy
*Attorney, Agent, or Firm*—Carol W. Burton; Holland & Hart LLP

[57] ABSTRACT

Compositions which include a mixture of CIPC and at least one substituted naphthalene are disclosed. The compositions of the present invention are adapted for inhibiting sprout growth in tubers. When so used, the preferred substituted naphthalene in the compositions of the present invention are dimethylnaphthalene (DMN) and diisopropylnaphthalene (DIPN). A method of applying a CIPC/naphthalene mixture is also disclosed. In a preferred embodiment of the method, tubers to be placed in storage are treated with a composition of CIPC and a substituted naphthalene utilizing thermal fogging techniques, with the average effective residue of CIPC on the tubers of from approximately 21 ppm to 2.5 ppm. In the preferred embodiment, the weight ratio of average effective residue of CIPC to the substituted naphthalene is from approximately 1:1 to 1:4. In a most preferred embodiment, a composition including CIPC and either DIPN or DMN is applied to tubers utilizing thermal fogging techniques, to obtain an average effective residue on the outer surface of the tubers of approximately 14 ppm CIPC and 14 ppm of the DIPN or DMN.

40 Claims, No Drawings

SPROUT INHIBITION COMPOSITIONS COMPRISING CHLORPROPHAM AND SUBSTITUTED NAPHTHALENES AND METHODS OF USING SAME

FIELD OF THE INVENTION

This invention relates to compositions used to inhibit sprouting of tubers. More particularly, this invention relates to CIPC and to substituted naphthalenes and to methods of applying same to tubers, especially to potatoes, to inhibit sprouting during storage.

BACKGROUND OF THE INVENTION

Sprout control of harvested tubers, in particular of potatoes, is an important part of potato storage which allows for subsequent distribution to potato processors for French fry production, and to grocery stores and restaurants of a satisfactory food product months beyond harvesting, skin formation and dormancy. Potato sprout control is particularly important to maintain the desired texture and sugar content of the harvested potatoes.

In potatoes, cell division and cell elongation of the tuber buds results in formation and emanation of sprouts from the tuber buds after the potato has entered a quiescent phase of dormancy that typically follows storage at or slightly above 45° F. Although tuber sprout formation can be suppressed by storage of the tubers at lower temperatures of from 38° to 39° F., the lower storage temperatures cause increased reducing sugar levels in the stored potatoes. Potatoes with increased levels of reducing sugars may turn brown when french fried, thereby producing an unacceptable food product.

To inhibit sprout formation in potatoes, synthetically derived sprout inhibitors, for example, tetrachloronitrobenzene, maleic hydrazide, and isopropyl-3-chlorophenylcarbamate (CIPC) also commonly referred to as chlorpropham, have been applied. CIPC is typically applied in one or two applications to the tubers to be stored using thermal fogging techniques. Conventional thermal fogging involving the application of CIPC into a stream of hot air or onto a hot surface of up to 1000° F., to produce a CIPC aerosol. The CIPC aerosol is circulated through potatoes piled in a potato storage building with the use of fans. Preferably the potatoes are firm rather than soft when treated with the CIPC aerosol, since a pile of softened potatoes may be substantially compressed, thereby impeding distribution of the aerosol. CIPC residue levels, will, however, typically decrease over time due to biodegradation, venting and atmospheric loss. To extend the effective sprout inhibiting capability of CIPC, further applications may be needed.

However, it is becoming increasingly desirable worldwide to decrease the application of synthetically derived substances to fruits and vegetables during growth, storage and shipping. In particular, residue levels of CIPC are subject to regulation. So, while CIPC has been utilized to inhibit sprout formation in tubers for decades, its toxicology has been questioned and it is one of a number of synthetically derived substances whose residue levels are of concern to the U.S. Environmental Protection Agency.

In order to decrease use of synthetically derived substances such as CIPC, naturally occurring biological control mechanisms and substances are actively sought. Naturally occurring sprout inhibitors are known. For example, U.S. Pat. No. 5,436,226 for NATURAL SUPPRESSION OF SPROUTING IN STORED POTATOES USING JAS-MONATES claims a method of inhibiting sprouting of tubers by exposure to various forms of jasmonic acid, at some of which are naturally occurring compounds.

Also by way of example, Canadian Patent No. 1,203,394 teaches the use of dimethylnaphthalene (DMN) and diisopropylnaphthalene (DIPN) as potato sprout inhibitors. However, this patent teaches the need for application of DMN and DIPN with an inert carrier which implies the utility of DMN and DIPN alone as the active ingredient. However, long term effectivity of DMN and DIPN as tuber sprout inhibitors at lower residue levels under less than ideal circumstances has not been fully established.

It is against this background that the significant improvements and advancements of the present invention have taken place.

OBJECTS OF THE INVENTION

It is the principal object of the present invention to inhibit sprouting of tubers during storage of the tubers in such a way as to decrease residual CIPC on tubers below conventional levels.

It is another object of the present invention to inhibit sprouting of tubers during storage using naturally occurring sprout inhibitors.

It is a further object of the present invention to inhibit sprouting of tubers during storage using conventional equipment.

It is a still further object of the present invention to inhibit sprouting of tubers in accordance with the aforementioned objects in such a manner that two months after treatment, at least half of the stored tubers are suitable for market.

SUMMARY OF THE INVENTION

In accordance with its major aspects, a composition specially adapted for inhibiting sprout formation of tubers during storage includes CIPC and a substituted naphthalene. In a preferred embodiment, the weight ratio of CIPC to the substituted naphthalene is from approximately 1:1 to 1:4. Preferred substituted naphthalenes are dimethylnaphthalene (DMN) and diisopropylnaphthalene (DIPN), and mixtures thereof.

In a preferred embodiment of the method of the present invention, an effective amount of a composition comprising CIPC and a substituted naphthalene is applied to the surface of potatoes, by, for example, thermal fogging, to form a residue on the outer surface of the potatoes. The CIPC and substituted naphthalene are provided in a preferred weight ratio of from approximately 1:1 to 1:4, to form an initial residue in which the CIPC is present at from approximately 14 ppm to approximately 2.5 ppm of the total tuber weight. The most preferred substituted naphthalenes for use with the method of the present invention are DIPN and DMN.

Employing the aforementioned method has resulted in substantial sprout control of Russet Norkota potatoes stored for over two months upon which an effective residue of CIPC and either DIPN or DMN of approximately 14 ppm each is applied.

A more complete appreciation of the present invention and its scope can be obtained from the following detailed description of presently preferred embodiments of the invention, and the appended claims.

DETAILED DESCRIPTION OF THE INVENTION

In accordance with the present application, it has been discovered that under the particular conditions described below, substituted naphthalenes, notably dimethylnaphthalene (DMN) and diisopropylnaphthalene (DIPN), when mixed with isopropyl-3-chlorophenyl-carbamate (CIPC) and applied to Russet Norkota potatoes, appear to enhance the sprout inhibiting capability of reduced amounts of CIPC for at least 2½ months. In view of the apparent inability of DMN and DIPN to inhibit sprouting of Russet Norkota potatoes under the particular conditions described below for the same period of time, the effectiveness of the combination was quite unexpected. The precise sprout inhibition mechanism of the CIPC/substituted naphthalene mixtures tested is not completely understood.

To evaluate the sprout inhibiting effectiveness of CIPC and substituted naphthalenes, alone and in mixtures of various concentrations, fully mature Russet Norkota potatoes were selected and treated. Russet Norkota potatoes were chosen because of their short dormancy and vigorous sprouting. Prior to treatment, the potatoes were stored in a dark, cool storage area to satisfy the dormancy period.

For each of the fifteen treatments summarized in Table I, 36 mesh bags, each containing ten Russet Norkota potatoes of from 4 to 10 ounces each, were placed in a non-metallic drum having an approximate capacity of 35 gallons. The total weight of 360 potatoes in each drum averaged 140.7 pounds.

The drums containing the mesh bags of potatoes were sealed and housed in a building in which temperature was maintained throughout the testing period at approximately 46° F. and approximately 96% relative humidity. Formed in in each drum was an inlet in which treated and/or untreated air was introduced to the drum contents, as described below. Also formed in each drum was an outlet at the top end of the drum in which treated and/or untreated air was exhausted from the drum and thence to the outside of the building:

For all drums except the control, the CIPC, substituted naphthalene, or CIPC and a substituted naphthalene was delivered to each drum through a stinger inserted in the input port of the drum and extending the length of the drum. Treatment levels were calculated based on milligrams (mg) of each of the CIPC, DIPN and DMN applied per kilogram (kg) of tubers treated, and reported in parts per million (ppm). Conventional thermal fogging techniques were used to generate the thermal fog delivered to the potatoes through the stinger. Return flow obtained from the output port was returned to the thermal fogger and recirculated through the stinger for five minutes. Each drum was then sealed for 24 hours after the application of the thermal fog. Then, for the next 140 days, 46° F. air having a relative humidity of 95% was circulated through the input port of each drum and exhausted out the output port of each drum to the outside of the building, at a rate of 0.5 cubic feet per minute on a three-hour on and a three-hour off schedule.

At 36 days, 77 days, 105 days, and 141 days after treatment, a sample of six of the 36 bags from each drum were removed, and the sixty total tubers from the six bags examined. Each eye on each tuber was counted and rated for sprout development, according to the scale described in TABLE I.

TABLE I

| RATING | EXTENT OF SPROUT DEVELOPMENT |
|---|---|
| 0 | No development |
| 1 | Sprout peeping (tissue is swelling; free tissue is evident) |

TABLE I-continued

| RATING | EXTENT OF SPROUT DEVELOPMENT |
|---|---|
| 2 | Sprout is up to 3 millimeters (mm) long |
| 3 | Sprout is >3 mm to 3 centimeters (cm) long |
| 4 | Sprout is >3 cm to 5 cm long |
| 5 | Sprout is >5 cm long |

The average sprout rating for each tuber was determined by dividing the total of the ratings for each tuber by the number of eyes on that tuber. A tuber having an average sprout rating of 1.5 or less was deemed suitable for fresh pack. As used herein, the term fresh pack indicates those potatoes which meet conventional standards set by groceries for the grade of potatoes sold as baking potatoes. The percentage of potatoes in each drum deemed suitable for fresh for each treatment at 36 days, 77 days, 105 days, and 141 days after treatment, was determined by dividing that quantity of the 60 potatoes sampled for each treatment and rated as suitable for fresh pack by 60 and multiplying by 100. The data obtained from the above tests is summarized in Table II.

TABLE II

| | | PERCENTAGE OF STORED POTATOES SUITABLE FOR FRESH PACK DAYS AFTER TREATMENT | | | |
|---|---|---|---|---|---|
| TREATMENT | LEVEL | 36 DAYS | 77 DAYS | 105 DAYS | 141 DAYS |
| CONTROL | 0 ppm | 17.86% | 0.00% | 0.00% | 0.00% |
| CIPC | 14 ppm | 85.92% | 4.09% | 0.08% | 8.23% |
| CIPC | 22 ppm | 82.14% | 50.00% | 59.83% | 79.86% |
| DIPN | 14 ppm | 52.91% | 0.00% | 0.00% | 0.00% |
| DIPN | 28 ppm | 3.02% | 0.00% | 0.00% | 0.00% |
| DIPN | 56 ppm | 1.35% | 0.00% | 0.00% | 0.00% |
| DMN | 14 ppm | 50.00% | 0.00% | 0.00% | 0.00% |
| DMN | 28 ppm | 32.90% | 0.00% | 0.00% | 0.00% |
| DMN | 56 ppm | 4.09% | 0.00% | 0.00% | 0.00% |
| CIPC + DIPN | 14 ppm 14 ppm | 93.30% | 67.10% | 11.70% | 35.66% |
| CIPC + DIPN | 14 ppm 28 ppm | 96.98% | 64.34% | 41.32% | 32.90% |
| CIPC + DIPN | 14 ppm 56 ppm | 27.56% | 20.14% | 11.70% | 6.70% |
| CIPC + DMN | 14 ppm 14 ppm | 95.91% | 52.91% | 15.69% | 27.56% |
| CIPC + DMN | 14 ppm 28 ppm | 88.30% | 35.66% | 25.00% | 22.52% |
| CIPC + DMN | 14 ppm 56 ppm | 91.77% | 61.53% | 47.09% | 52.91% |

As is summarized in Table II above, tubers treated with substituted naphthalenes alone, whether at 14, 28 or 56 ppm residue levels, were completely unsuitable for fresh pack at 77, 105 and 141 days after treatment. Untreated (control) tubers were equally unsuitable for fresh pack at the same time intervals.

As summarized in Table II, tubers treated with CIPC in accordance with the method described above to an average residue level of 14 ppm CIPC, resulted in percentage of tubers suitable for fresh pack at 77, 105 and 141 days after treatment at levels of 4.09%, 0.08% and 8.23%, respectively. An average percentage of stored tubers suitable for fresh pack of less than 10%—a percentage of tubers unsuitable for fresh pack of greater than 90%—is clearly unacceptable when the tubers are being stored for fresh pack sale.

Only when the tubers were treated with an average residue level of CIPC alone of 22 ppm, did the percentages of tubers suitable for fresh pack at all sampling dates after treatment average at or above 50%. As is summarized in Table II, at 35, 77, 105 and 141 days after treatment, tubers so treated averaged 82.14%, 50.00%, 59.83% and 79.86% suitable for fresh pack, respectively.

However, what was unexpected, and as is summarized above in Table II, the application of a mixture of CIPC and DIPN to the tubers to obtain average residue levels of 14 ppm CIPC and 14 ppm DIPN, resulted in a total percentage of fresh pack at 77, 105 and 141 days after treatment, 67.10%, 11.70% and 35.66%, respectively, which were substantially greater than the sum of the fresh pack percentages of each treatment separately, i.e., 4.09%+0.0%, 0.08%+0.00%, and 8.23%+0.00%, respectively. Similarly the application of a mixture of CIPC and DIPN to the tubers obtain residue levels of 14 ppm CIPC and 28 ppm DIPN, resulted in a total percentage of fresh pack at 77, 105 and 141 days after treatment, 64.34%, 41.32% and 32.90%, respectively, substantially greater than the sum of the fresh pack percentages of each treatment separately, i.e., 4.09%+0.0%, 0.08%+0.00%, and 8.23%+0.00%, respectively.

In an analogous manner, and as also summarized above in Table II, the application of a mixture of CIPC and DMN to the tubers obtain residue levels of 14 ppm CIPC and 14 ppm DMN, resulted in a total percentage of fresh pack at 77, 105 and 141 days after treatment, 52.91%, 15.69% and 27.56%, respectively, which were substantially greater than the sum of the fresh pack percentages of each treatment separately, i.e., 4.09%+0.0%, 0.08%+0.00%, and 8.23%+0.00%, respectively. Similarly, the application of a mixture of CIPC and DMN to the tubers obtain residue levels of 14 ppm CIPC and 28 ppm DMN, resulted in a total percentage of fresh pack at 77, 105 and 141 days after treatment, 35.66%, 25.00%, 22.52%, respectively which were greater than the sum of the fresh pack percentages of each treatment separately, i.e., 4.09%+0.0%, 0.08%+0.00%, and 8.23%+0.00%, respectively. In a likewise manner, the application of a mixture of CIPC and DMN to the tubers obtain residue levels of 14 ppm CIPC and 56 ppm DMN, resulted in a total percentage of fresh pack at 77, 105 and 141 days after treatment, 61.53%, 47.09% and 52.91%, respectively, also greater than the sum of the fresh pack percentages of each treatment separately, again 4.09%+0.0%, 0.08%+0.00%, and 8.23%+0.00%, respectively.

Thus it can be seen that CIPC residue levels of 22 ppm are not required when CIPC is applied in conjunction with a substituted naphthalene of the present invention. When applied in conjunction with a substituted napthalense of the present invention, a preferred CIPC level is from 21 ppm to 2.5 ppm, with the most preferred CIPC level of from 17 ppm to 14 ppm. It should be understood that as used herein, the term substituted naphthalene is understood to encompass, but is not limited to, methylated naphthalenes, ethylated naphthalenes, isopropylated naphthalenes, carboxylated naphthalenese and halogenated naphthalenes.

Moreover, in addition to utilizing thermal fogging techniques to produce and apply the improved sprout inhibiting compositions of the present invention, other conventional application methods may be employed. For example, potatoes may be dipped into a solution or solutions comprising the improved sprout inhibiting composition of the present invention. Also by way of example, the improved sprout inhibiting compositions of the present invention may be sprayed in aerosol form at temperatures less than the elevated temperatures utilized with thermal fogging, for example at ambient temperatures.

Presently preferred embodiments of the present invention and many of its improvements have been described with a degree of particularity. It should be understood that this description has been made by way of preferred examples, and that the invention is defined by the scope of the following claims.

What is claimed is:

1. A composition adapted for inhibiting sprout formation in tubers during storage, comprising:

CIPC (chlorpropham); and a substituted naphthalene.

2. The composition of claim 1 wherein the substituted naphthalene is DIPN (diisopropylnaphthalene).

3. The composition of claim 1 wherein the substituted naphthalene is DMN (dimethylnaphthalene).

4. The composition of claim 1 wherein the substituted naphthalene is selected from the group consisting of DIPN, DMN and methyl naphthalene.

5. The composition of claim 1 wherein the weight ratio of CIPC to substituted naphthalene is from 1:1 to 1:4.

6. The composition of claim 2 wherein the weight ratio of CIPC to DIPN is from 1:1 to 1:4.

7. The composition of claim 3 wherein the weight ratio of CIPC to DMN is from 1:1 to 1:4.

8. The composition of claim 4 wherein the weight ratio of CIPC to the selected substituted naphthalene is from 1:1 to 1:4.

9. A method of inhibiting sprout formation in tubers during storage, comprising the steps of:

applying an effective amount of a composition comprising CIPC and a substituted naphthalene to the outer surface of the tubers to form a residue thereon; and storing the tubers upon which the residue has been formed.

10. The method of claim 9 wherein the CIPC is present in the residue, on average, at from approximately 21 ppm to approximately 2.5 ppm.

11. The method of claim 9 wherein the substituted naphthalene includes DIPN.

12. A method of claim 11 wherein the CIPC is present in the residue at from approximately 21 ppm to approximately 2.5 ppm.

13. A method of claim 11 wherein the CIPC and DIPN are present in the residue in a weight ratio of from approximately 1:1 to 1:4.

14. A method of claim 12 wherein the CIPC and DIPN are present in the residue in a weight ratio of from approximately 1:1 to 1:4.

15. The method of claim 9 wherein the substituted naphthalene includes DMN.

16. A method of claim 15 wherein the CIPC is present in the residue, on average, at from approximately 21 ppm to approximately 2.5 ppm.

17. A method of claim 15 wherein the CIPC and DMN are present in the residue in a weight ratio of from approximately 1:1 to 1:4.

18. A method of claim 16 wherein the CIPC and DMN are present in the residue in a weight ratio of from approximately 1:1 to 1:4.

19. A method of inhibiting sprout formation in tubers during storage, comprising the steps of:

providing a composition comprising CIPC and a substituted naphthalene to form a sprout inhibiting composition;

applying an effective amount of the sprout inhibiting composition to the outer surface of the tubers to form treated potatoes; and storing the treated tubers.

20. The method of claim 19 wherein the weight ratio of CIPC to substituted naphthalene in the composition is from approximately 1:1 to 1:4.

21. The method of claim 19 wherein the substituted naphthalene is selected from the group consisting of DIPN, DMN and methyl naphthalene.

22. The method of claim 21 wherein the weight ratio of CIPC to the selected substituted naphthalene in the composition is from approximately 1:1 to 1:4.

23. The method of claim 19 wherein the substituted naphthalene includes DIPN.

24. The method of claim 23 wherein the weight ratio of CIPC to DIPN in the composition is from approximately 1:1 to 1:4.

25. The method of claim 19 wherein the substituted naphthalene includes DMN.

26. The method of claim 25 wherein the weight ratio of CIPC to DMN in the composition is from approximately 1:1 to 1:4.

27. The method of claim 19 wherein the applying step further includes the step of dipping the tubers in the sprout inhibiting composition.

28. The method of claim 27 wherein the substituted naphthalene is selected from the group consisting of DIPN and DMN.

29. The method of claim 27 wherein the weight ratio of CIPC to substituted naphthalene in the composition is from approximately 1:1 to 1:4.

30. The method of claim 19 wherein the applying step further includes the steps of:

aerating the sprout inhibiting composition to form a sprout inhibiting aerosol; and applying the sprout inhibiting aerosol to the tubers to form treated potatoes.

31. The method of claim 30 wherein the substituted naphthalene is selected from the group consisting of DIPN and DMN.

32. The method of claim 30 wherein the weight ratio of CIPC to substituted naphthalene in the composition is from approximately 1:1 to 1:4.

33. A method of inhibiting sprout formation on tubers during storage, comprising the steps of:

applying CIPC to the tubers in an amount effective to form a residue thereon and inhibit sprout formation therefrom;

applying a substituted naphthalene to the tubers in an amount effective to form a residue thereon and to inhibit sprout formation therefrom; and storing the tubers for a period of time, wherein the CIPC and substituted naphthalene residues are both present for at least a portion of the period of time the tubers are stored.

34. The method of claim 33 wherein the substituted naphthalene includes DIPN.

35. The method of claim 34 wherein the CIPC and DIPN are applied to the tubers in a weight ratio of from approximately 1:1 to 1:4.

36. The method of claim 33 wherein the substituted naphthalene includes DMN.

37. The method of claim 36 wherein the CIPC and DMN are applied to the tubers in a weight ratio of from approximately 1:1 to 1:4.

38. The method of claim 33 wherein the substituted naphthalene is selected from the group consisting of DIPN, DMN and methyl naphthalene.

39. The method of claim 38 wherein the CIPC and the substituted naphthalene are applied to the tubers in a weight ratio of from approximately 1:1 to 1:4.

40. The method of claim 33 wherein the CIPC is applied and initially present in the residue, on average, at from approximately 21 ppm to approximately 2.5 ppm.

* * * * *